United States Patent [19]

Ruehling

[11] Patent Number: 5,059,419

[45] Date of Patent: Oct. 22, 1991

[54] STREPTOCOCCUS SUIS ANTISERUM AND ITS USE IN TREATING STREPTOCOCCUS SUIS INFECTIONS

[75] Inventor: Roger H. Ruehling, Inwood, Iowa

[73] Assignee: Grand Laboratories, Inc., Larchwood, Iowa

[21] Appl. No.: 204,270

[22] Filed: Jun. 9, 1988

[51] Int. Cl.$^5$ .................. A61K 39/40; A61K 39/02
[52] U.S. Cl. ..................................... 424/87; 424/88; 424/92
[58] Field of Search ............................ 424/87, 88, 92

[56] References Cited

U.S. PATENT DOCUMENTS

| | | | |
|---|---|---|---|
| 3,992,521 | 11/1976 | Le Minor | 424/87 |
| 4,096,244 | 6/1978 | Newson et al. | 424/85.8 |
| 4,367,221 | 1/1983 | Kasper | 424/87 |
| 4,367,222 | 1/1983 | Kasper | 424/87 |
| 4,748,018 | 4/1988 | Stolle et al. | 424/87 |

OTHER PUBLICATIONS

Elliott, et al., J. Exp. Med. 148: 1699–1704 (1978) The Type–Specific Polysaccharides of Streptococcus suis.
Agarwal, et al., J. Hyg. Camb. 67: 491–503 (1969) The Immunity of Adult Pigs Investigated . . . Test.
Perch, et al., J. Clin. Micro. 17: 993–96 (1983) Serology of Capsulated Streptococci . . . Streptococcus suis.
Windsor, et al., J. Hyg. Camb. 75: 69–78 (1975) Streptococcal Infection in Young Pigs.
Elliott; J. Hyg. Camb. 64: 205–220 (1966) Streptococcal Infection in Young Pigs.
De Morr; Antonic van Leeuwenhoek 29: 272–280 (1963) Septicaemic Infections in Pigs . . . Designated R, S and T.
Sanford; 26th Annual George A. Young Conf. and 25th Annual Nebraska SDF Conf. (1985 Proceedings).
Kilpper–Bals, et al., Int'l. Journal of Systematic Bacteriology; 37:160–62 (1987) Streptococcus . . . nom. rev.
Perch, et al., Acta path. microbiol. scand. B.89: 167–171 (1981) Biochemical . . . and RS Streptococci.
Azuma, et al., Nat'l. Inst. Anim. Health 23: 117–126 (1983) Streptococcus R . . . in Pigs in Japan.
Elliott, et al., J. Hyg. Chamb. 85: 275–285 (1980) Streptococcal Infection . . . meningitis in Pigs.
Castrucci, et al., Comp. Immunol. Microbiol. Infec. Dis. 7(3–4)(171–178 (1984); Biosys No. 80014153; Comparative Study of Rotavirus Strains of Bovine and Rabbit Origin.

Primary Examiner—Garnette D. Draper
Assistant Examiner—Abdel A. Mohamed
Attorney, Agent, or Firm—Iver P. Cooper

[57] ABSTRACT

An antiserum for the prevention and treatment of Streptococcus suis infections in piglets is obtained by hyperimmunization of an equine.

17 Claims, 1 Drawing Sheet

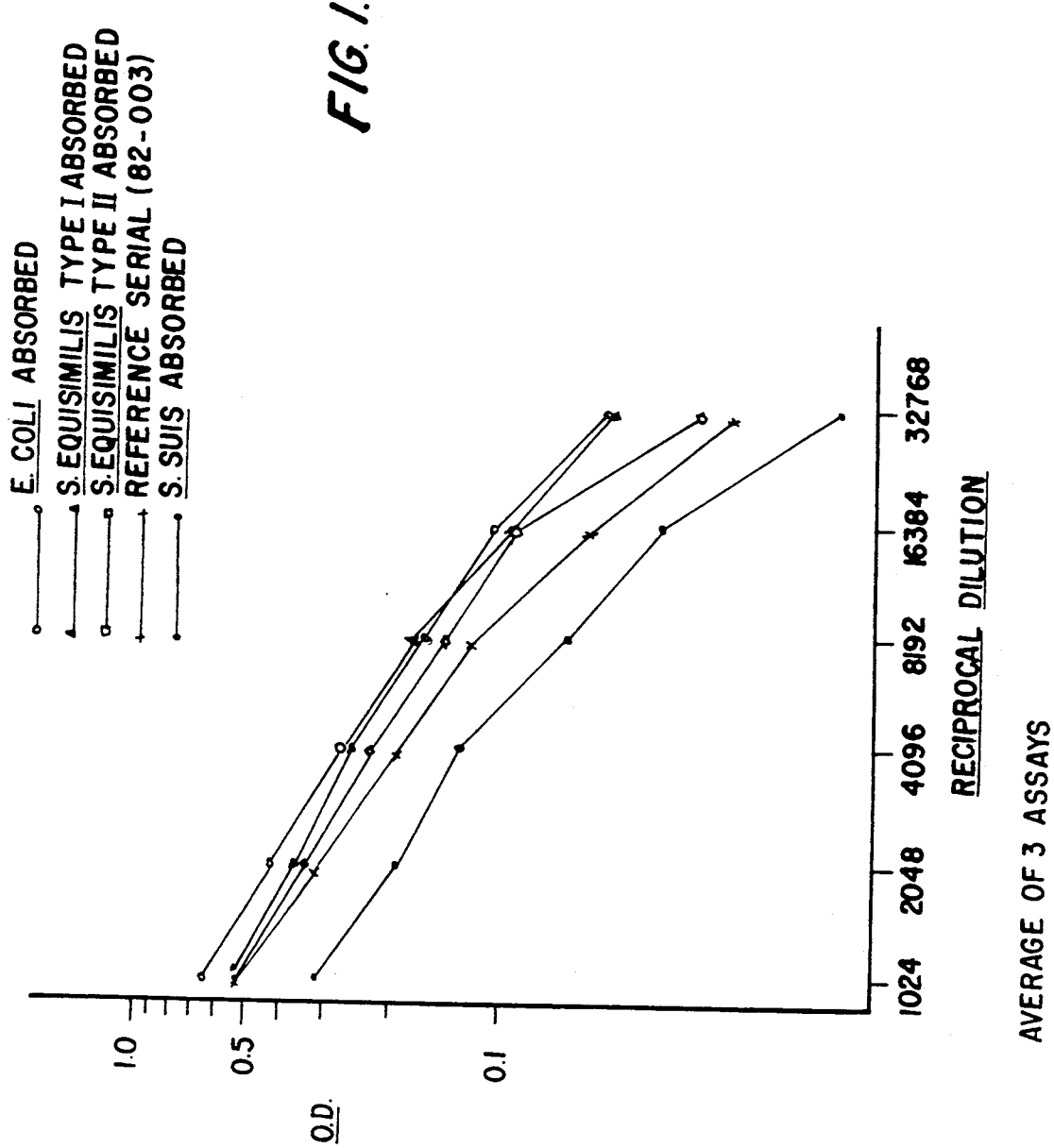

STREPTOCOCCUS SUIS ANTISERUM AND ITS USE IN TREATING STREPTOCOCCUS SUIS INFECTIONS

BACKGROUND OF THE INVENTION

1. Field of the Invention

This invention relates to the prevention and treatment of *Streptococcus suis* infections by means of an antiserum obtained by hyperimmunization of horses.

2. Information Disclosure Statement

DeMoor, *Antonie van Leeuwenhoek*, 29:272-280 (1963) reported the discovery of three new serological groups of Streptococci which were responsible for septicemic infections in pigs. These three groups, denoted Lancefield R, S and T, exhibited beta-hemolysis on horse blood agar and acid production from inulin. The serologically distinctive antigens were cell wall polysaccharides.

Elliot, *J. Hyg. Camb.*, 64: 205-212 (1966) studied the causative agent of certain outbreaks of streptococcal infection. This agent, "PM streptococcus," was serologically identical to Field's strain 428 and De Moor's group S streptococcus, but Elliot assigned them to Lancefield Group D. However, in view of the differences between PM streptococcus and other group D organisms, Elliot proposed designating a new subgroup, *Streptococcus suis*, and assigning the PM strains to "Capsular Type 1." De Moor's group R were later designated "Capsular Type 2." See Windsor and Elliot, *J. Hyg. Camb.*, 75: 69-78 (1975). Other types have since been identified. See Perch, et al., *J. Clin. Microbiol*, 17(6): 993-996 (1983). *Streptococcus suis* infections in pigs and humans have been reported in Europe and other countries as early as 1954. An increased awareness of the problem by practitioners and diagnosticians in the United States has recently resulted in a dramatic rise in case reports of *S. suis* problems in pigs of all ages. The disease may vary from subclinical infection to death. Some conditions and disease attributed to *S. suis* infections in swine are as follows:

| | |
|---|---|
| Meningitis | "Fading pig syndrome" |
| Arthritis | Fibrinopurulent pericarditis |
| Pneumonia | Haemorrhagia necrotizing myocarditis |
| Septicemia | Vegetative valvular endocarditis |
| Vaginitis | Abortion |

Clinical signs of the infection include various combinations of anorexia, depression, reddening of the skin, fever, incoordination, swollen joints, blindness, deafness, and lameness. In peracute cases of septicemia or meningitis, there may be no premonitory clinical signs and pigs may just be found dead.

*Streptococcus suis* is commonly found in the upper respiratory tract and tonsils of pigs in most areas of the world in which swine are raised. Within an infected herd, virtually all pigs carry the organisms in their tonsillar crypts, and farrowing sows probably transmit the organism to young pigs through nasal contact. The bacterium may survive in feces for a week and in decomposing carcasses for almost 2 weeks. Fortunately, the organism is highly susceptible to most cleaning and disinfecting agents. Hadley and Enright, *Vet. Res.* 114:585-87 (1984).

Eradication through depopulation has been suggested, but most veterinarians recommend control by improving management practices and administering antibiotics when necessary. The organism is susceptible to penicillin in vitro, and antibiotic treatment is usually effective in acute cases, but is not necessarily favorable in chronic cases. Control by in-feed medication is only economic on the more severely affected farms. *S. suis* can persist in the tonsils in the presence of therapeutic levels of antibiotics and can persist in the environment for prolonged periods. Good management techniques may minimize the risks of *S. suis* infections in swine herds. It has been suggested to avoid overcrowding, poor ventilation, and other stressful conditions in the pig houses, especially when young pigs are mixed and moved to the nursery. All-in/all-out rearing as well as cleaning and disinfecting the premises between groups may help in control of outbreaks Erickson, *JAVMA* 191(11):1391-93 (1987).

Azuma, et al., *Nat. Inst. Anim. Health Q.* (Jpn.) 23:117-126 (1983) prepared antisera against *Strep. suis* by culturing the organism in a Todd-Hewitt broth, inactivating with pepsin, and inoculation the bacterin intravenously into rabbits on a daily basis for 12 successive days. The antisera were used only for serological typing. Perch likewise prepared anti-*Strep. suis* antisera by immunization of rabbits; again, there was no teaching of therapeutic or prophylactic utility.

Elliot reported that serum of piglets convalescent from *Str. suis* type 1 infections could protect susceptible animals from infection with "homologous streptococci." Piglets and horses, of course, are "heterologous."

The hyperimmunization of a horse with *Escherichia coli* or Salmonella, both gram negative rod-type bacteria, in order to obtain immune serum for use in man is known. Le Minor, U.S. Pat. No. 3,992,521. However, this technique has not been used in the preparation of *Streptococcus suis* (gram positive cocci-type bacteria) antiserum, and the use of such antiserum in immunization has not been reported.

SUMMARY OF THE INVENTION

It has now been discovered that an antiserum effective in the prevention and treatment of *Streptococcus suis* infections may be prepared by hyperimmunization of horses. No other *S. suis* antiserums are commercially available for immunization purposes. The antiserum is preferably administered by the intramuscular route.

The appended claims are incorporated by reference herein as a description of the preferred embodiments.

BRIEF DESCRIPTION OF THE DRAWINGS

FIG. 1 compares the optical density of supernatant after absorption of the hyperimmune antiserum of the present invention (Ref. Serial 82-003) by *E. coli*, *S. suis*, and *S. equisimilis* Type I and II cells.

DETAILED DESCRIPTION OF THE INVENTION

Example 1: Preparation of Antigen

A *Streptococcus suis* strain is cultivated in any suitable culture medium, preferably an enriched Todd-Hewitt broth (ETHB) containing the following ingredients per liter of distilled water:

| | |
|---|---|
| Heart Peptone | 3.1 g |
| Casein yeast/Peptone | 20.0 g |
| Sodium Chloride | 2.0 g |

| -continued | |
|---|---|
| Disodium Phosphate | 0.4 g |
| Sodium Carbonate | 2.5 g |
| Dextrose | 2.0 g |
| Yeast Extract | 10.0 g |
| *Casamino Acids | 2.0 g |
| *Glycerin | 2.0 ml |
| *Tween 80 | 2.0 ml |

The asterisks identify the three components which are preferably added to a conventional Todd-Hewitt broth and are believed to promote expression of an M-protein-like substance. This medium was inoculated with a 18-24 hr. culture of *S. suis* serotype ½. The culture was grown aerobically for 5 hours at 37° C. at a pH between 6.2 and 7.4 in a 10 liter fermenter or 2 l flask. Uniformly good cultures are obtained with 5 hours growth at 37° C. using 5 to 16% inoculum. Each ml of such a culture will preferably yield an $OD_{600}$ of approximately 5.2 using a Bausch and Lomb Spectronic 70.

Cultures may be inactivated by the addition of 37% formaldehyde to a final concentration of 0.25-0.5% (2.5 ml-5.0 ml of 37% formaldehyde/liter of culture) depending on antigen yield and incubated at 37°±2.0° C. for 12–72 hours. The formaldehyde is added to the culture by pumping or by gravimetric addition when the culture reaches peak antigen production.

After incubation, cultures are sampled and tested for inactivation by inoculation into sterile medium and incubated for at least 24 hours at 37°±2.0° C. Cultures showing viable growth may have formaldehyde levels readjusted up to 0.5% and may be reincubated, sampled and tested until inactivation is complete.

Noninactivated culture was held as live culture nonadjuvanted inoculum and stored frozen at ≦20° C.

Either inactivated (killed) or live *Streptococcus suis* may be used as the antigen in the production of the desired antiserum. While the invention is not limited to the use of any particular inactivating agent, the agent preferably is formalin, sodium lauryl sulfate, or heat. The invention is not limited to the use of any particular *Strep. suis* strain, but I employed GL-42, obtained from C. Gates of Brookings, S. Dak., which is of serotype ½. The term "source of *Streptococcus suis* antigen" in the appended claims embraces whole live bacterial cells, whole inactivated cells, cell-free antigenic extracts, and wholly or partially purified antigens.

Inactivated antigen may be used with, or less preferably without, an adjuvant. Any adjuvant may be used, but aluminum hydroxide and peanut oil are preferred. Formulae for two preferred bacterins are set forth below:

| | |
|---|---|
| AlOH Bacterin | |
| Antigen | 10,000 ml |
| AlOH | 1,500 ml |
| Antibiotic | 11.5 ml |
| Thimerosal (10%) | 11.5 ml |
| Formaldehyde (37%) | as needed |
| Oil Emulsion Bacterin | |
| Antigen | 5,000 ml |
| Peanut Oil | 5,000 ml |
| Antibiotic | 10 ml |
| Thimerosal (10%) | 10 ml |
| Formaldehyde (37%) | as needed |

Other oils such as mineral oil may be wholly or partially substituted for peanut oil, e.g., using a pepsin extract adjuvanted in 45% peanut oil and 5% mineral oil.

M-protein-like substance (which is believed to be produced due to the enriched Todd-Hewitt broth set forth above) may be extracted with hyaluronidase, purified by molecular sieve chromatography, and used as an antigen in an ELISA for *Strep. suis* antibodies.

This substance is acid and heat stable, can be extracted with low levels of pepsin, hyaluronidase or mytanolysin, or acid and heat, and is a virulence factor. For M-protein or M-antigen in Streptococci, See Aggarwal, et al., J. Hyg. Camb., 67: 491 (1969); Timoney, WO 87/00436 (1987); Usdin, U.S. Pat. Nos. 3,793,150 and 3,852,420; Brown U.S. Pat. Nos. 4,529,581 and 4,582,798.

Example 2: Hyperimmunization of Horses

Merely immunizing an animal typically requires only 1–3 vaccinations spaced weeks apart. Normally, it will take at least four vaccinations to hyperimmunize an animal, and use of at least seven vaccinations is preferred. Ten to twenty immunizations are especially preferred. The antigen is preferably administered on a periodic (daily, weekly, or biweekly especially weekly) basis, but intervals between immunizations may vary. On occasion, an immunization may be skipped to give the animal a chance to rest. Frequency of immunization and the product used for immunization may be varied depending upon individual animal response.

Preferably, inactivated antigens are administered intramuscularly or subcutaneously, and live bacteria are given intravenously. Immune sera from different animals may be blended to obtain a final product with the desired potency.

Four horses were each hyperimmunized according to a different protocol.

Horse 2×11 was immunized subcutaneously only with formalin killed whole cell in aluminum hydroxide. The first two weekly immunizations were 10 and 15 cc, respectively. All subsequent immunizations were 20 cc each. A total of 23 injections were carried out over a 27 week period.

Horse 3×11 was immunized according to a similar protocol, but a total of 26 injections were spread over 28 weeks.

Horse 4×11 had a somewhat different experience. The first ten weekly doses were of 5 cc of a pepsin extract in an oil emulsion. Eight more doses spread over weeks, were of formalin killed whole cell in AlOH. All doses were administered subcutaneously.

Horse 5×11 was placed under yet another protocol. In weeks 1 and 2 it received 10 cc and 15 cc, respectively, subcutaneously, of the formalin killed whole cell in AlOH. In weeks 3–6 it was given 20 cc. In week 7, Horse 5×11 was immunized subcutaneously with 2 cc of live frozen *Strep. suis* strain GL 42. Another 2 cc were given in week 8, this time intravenously. This was followed in weeks 9–22 with 5 cc of the live GL42, still intravenously. Four more such doses were rendered over weeks 23–28. All horses were titered by ELISA.

The serum from horses 2×11, 3×11, 4×11 and 5×11 was combined.

Example 3: Preparation of the Antiserum

Blood was collected, agitated, and the fibrin removed using aspectic technique. 0.25 ml of 16.6% Sodium Citrate was added per pound of blood collected. The blood was stored at 4° C. for 24 hours and the serum was harvested with the aid of sterile tubing and peristaltic pumps at a transfer station. The following preservatives were then added.

| Ingredient | Final Concentration |
| --- | --- |
| 005.0% Phenol | 10.00% |
| 100 mg/ml Oxytetracycline | .03% |
| 010.0% Thimerosal | .30% |
| Antifoam | .07% |

The serum was then filled into sterile 100 ml plastic vials and gamma irradiated receiving at least 2.5, but less than 4.0M rad absorbed dose. This product constitutes the antiserum of the present invention.

Example 4: Use of the Antiserum

To prove the effectiveness of the antiserum prepared as just described, newborn piglets of mixed breed with no known history of disease or vaccination to *Str. suis* were divided into two groups. One group (35 piglets) served as controls in that they did not receive antiserum. The second group (40 piglets received 2.0 ml antiserum intramuscularly at 2.0-8.5 hours of age. All piglets were allowed to suckle ad libitum and were challenged by the intravenous route with $4.33 \times 10^4$–$4.42 \times 10^5$ cfu/dose (*Str. suis* type ½) at 17-24 hours after antiserum administration. Each piglet was observed daily (for 14 days) for clinical signs. The following values were assigned to the clinical symptoms.

| Lameness/quarter | Eyes |
| --- | --- |
| 0 - no lameness | 0 - no symptoms |
| 1 - slight limp | 2 - puffy and swollen |
| 2 - pronounced limp | 4 - swollen shut/unable to open |
| 3 - reluctant to bear weight | |
| 4 - paralysis | |
| 2 - slight swollen joint | |
| 4 - large swollen joint | |
| Other | |
| 10 - lethargic/septicemia | |
| 4 - Hunch back stance | |
| 50 - death | |
| 4 - tremors | |

Table 1 lists the percent mortality, total clinical scores, and average clinical scores for treated and control piglets.

TABLE 1

Results Obtained Following Challenge of Piglets with Virulent *Streptococcus suis*

| Group | n | Mortality (%) | Total Clinical Score | Average Clinical Score |
| --- | --- | --- | --- | --- |
| Treatment | 40 | 7/40 (17.5) | 3794 | 94.85 |
| Control | 35 | 12/35 (34.3) | 6979 | 199.40 |
| P | — | *.054 | — | **.012 |

*2 × 2 Contingency Test
**Student t Test

It is clear from the foregoing table that intramuscular administration of *Str. suis* antiserum significantly reduced the mortality and morbidity of the challenged piglets.

Control and treatment piglets from each litter (Table 1) which died as well as randomly selected surviving control and treatment piglets were necropsied. The brains were cultured for bacteria using 5% sheep blood agar plates. Plates which demonstrated hemolytic activity and morphology typical of *Str. suis* were considered positive. Random reisolated cultures typical of *Str. suis* were confirmed using biochemical methods.

Random reisolated cultures demonstrating acid production from dextrose, inulin, sucrose and trehalose, but not from mannitol or sorbitol were considered confirmatory for *S. suis*. The results are shown in Table 2 below.

TABLE 2

Results of Bacteriologic Sampling of the Brain at Necropsy

| Group | No. Positive/Total Plated | (%) |
| --- | --- | --- |
| Treatment | 11/16 | (68.8) |
| Control | 17/17 | (100.0) |
| P | *.018 | |

*2 × 2 Contingency Test
**Student t Test

It is evident that a virulent challenge occurred in that *Str. suis* was recovered from the brain of all 17 control piglets necropsied. The protective effect of the vaccine is shown by reduced presence of *Str. suis* in the brains of treatment piglets.

The antiserum is preferably administered intramuscularly within 24 hours of birth. Oral, intraperitoneal and axillary administration did not provide the desired results.

In another study, four week old pigs involved in a outbreak of *Strep. suis* infection were given 5 ml antiserum intramuscularly. The outbreak was halted without any adverse experiences.

Example 5: Evaluation of ELISA for Streptococcus Suis Antibodies

An ELISA for *Streptococcus suis* antibodies has been developed. This ELISA may be used to evaluate the potency of *Strep. suis* hyperimmune sera.

Our reference serial 82-003 was the antiserum used in our host animal efficacy study.

Twofold serial dilutions of the reference serial and prelicensing serials were compared using ELISA. Immulon 2 plates were coated with *S. suis* antigen overnight at 4° C. The wells were then blocked with bovine serum albumin for 1½ hours at room temperature. Serial dilutions of the reference serial and prelicensing serial were added to the wells and allowed to incubate at room temperature for 1½ hours. Rabbit anti-horse IgG peroxidase conjugate was added to the wells and allowed to incubate for 1½ hours at room temperature. ABTS/-$H_2O_2$ was added to each well and allowed to develop for 10 minutes at room temperature before the reaction was stopped with the addition of stopping buffer. All wells were washed 3–4 times with washing buffer between each step. The ELISA reader was blanked on a negative well (received washing buffer instead of antiserum) and the O.D. of each well was read and recorded.

Specificity was demonstrated by adsorbing the reference serial with homologous and heterologous strains of bacteria (*Streptococcus suis, Streptococcus equisimilis* Type I, *Streptococcus equisimilis* Type II, and *Escherichia coli.* Two ml of the reference serial was absorbed with 0.4 ml of packed cell slurry of each organism for 1½ hours at 37° C. The antisera were centrifuged and the supernatants were used in the assay.

The results in FIG. 1 demonstrate ELISA test specificity. Only *S. suis* adsorbed out antibody.

Example 6: Characterization of AntiSerum

A. ELISA was used to determine if the present invention's *S. suis* antiserum (raised against serotype ½) contains Ab against serotypes 2, 4, 7, and 8. The results were as follows:

|  | Titer | | | | |
| --- | --- | --- | --- | --- | --- |
|  | 2 | 4 | 7 | 8 | ½ |
| Normal Horse Serum | 256 | 128 | 16 | 64 | NT |
| Serial 82-004 | >4096 | >4096 | 128 | 256 | 2048 |

The results indicate that our *S. suis* antiserum contains Ab against all 4 serotypes, especially serotypes 2 and 4. The Ab being measured is not against the Elliot type specific capsular carbohydrate.

B. ELISA and capillary precipitation was used to determine if the Ab being measured is against the group D antigen. The group D antigen used was from Difco.

|  | Horse 02 | Serial 82-004 | D Antitoxin (Difco) |
| --- | --- | --- | --- |
| ELISA Titer | 32768 | 8192 | 640 |
| Precipitation | − | − | + |

The results indicate that the Ab being measured is not against the group antigen. Previous tests in ELISA with chromatographically purified protein suggested that an M-protein-like substance was being measured in the ELISA system. If this is true, than serotypes 2, 4, 7, and 8 contain the same M-protein-like substance. If antibody to the M-protein-like substance is protective then our antiserum raised against serotype ½ should be protective for 2, 4, 7, and 8 serotypes. We have had field indications that our antiserum was an effective treatment against serotype 7.

Bibliography

1. Field, H. I., Buntain D. and Done, J. T.; Studies on pig mortality. I. Streptococcal meningitis and arthritis, Vet. Rec. 66: 453–455. 1954.

2. DeMoor C. E.; Septicaemic infection in pigs, caused by hemolytic streptococci of new lancefield groups designated R, S and T. Antonie Van Leeuwenhoek, 29: 272–280. 1963.

3. Elliott S. D.; Streptococcal infection in young pigs. I. An immunochemical study of the causative agent (PM Streptococcus). J. Hyg. Camb., 64: 205–212. 1966.

4. Engel H. W. B.; Narucka U. and Westendorp J. F.; Streptococcen by Schlachtvarkens (Streptococci in slaughtered pigs). Trijdschr. Diergeneesk, deel 99, afl. 22: 1162–1170, 1974.

5. Jones J. E. T.; The serological classification of streptococci isolated from diseased pigs. Br Vet. J. 132: 163–171, 1976.

6. Kunter E. and Wittig W.; R-and-S-Streptokokken-Infektionen heim Schwein. Arch. Exper. Vet. Med. Leipzig 30: 211–216, 1976.

7. Pedersen K. B., Slot P. and Schou S.; Udbrud streptokokmeningitis i en dansk svinebesaetnins (Outbreak of streptococcal meningitis in a Danish herd of piglets). Dans Vet. Tidsskr 60:812–813, 1977.

8. Azuma R.; Hana F., Oonuma Y., and SUGIMOTO C.; Streptococcus R. (*Streptococcus suis* Type II) Infection in Pigs in Japan, Natl. Inst. Anim. Health Q. (Jpn) 23:117–126, 1983.

9. Twort C. H. C.; Group R streptococcal meningitis (*Streptococcus suis* Type II): a new industrial disease? British Medical Journal 282: 253–524, 1981.

10. Agass M. J. B., et al.; Meningitis and endophthalmitis caused by *Streptococcus suis* Type II (group R), British Med J., 16: 167–168, 1977.

11. Chattopadhyay, B. Group R Streptococcus Infection Amongst Pig Meat Handlers—A Review, Publ. Hlth. Lond. 93: 140–142, 1979.

12. Woo J., *Streptococcus suis* meningitis in man in Hong Kong. Trans. Roy, Soc. Trop. Med. Hyg. 80: 848–849, 1986.

13. McLendon B. F., Bron A. J., and Mitchell C. J.; *Streptococcus suis* Type II (group R) as a cause of endophthalmitis. Br. J. Ophthalmology 62: 729–731, 1978.

14. Koehne G., Maddox R. I., and Cornell W. D.; Lancefield Group R Streptococci Associated with Pneumonia in Swine. Am J. Vet Res. 40, 11 1640–1641, 1979.

15. Hoffman, I. J., and Hendersen I. M.: The significance of *Streptococcus suis* in swine disease: Clinical, Pathologic and Bacteriologic data from a two year study. Amer Assn Vet Lab Diag, 28th Annual Proceedings, 201–210, 1985.

16. Erickson D. E. and Doster A. R.; *Streptococcus suis* infection of swine in Nebraska. Dept. Vet. Sci., University of Nebraska, Lincoln.

17. Arends J. P., Haretwig N., Rudolphy M, et al.; Carrier rate of *Streptococcus suis* capsular type 2 in palatine tonsils of slaughtered pigs. J. Clin. Microbiol., 20, (5) 945–947, 1984.

18. Clifton Hadley F. A.; and Enright M. R.; Factors affecting the survival of *Streptococcus suis* Type 2. Vet Res. 114:585–587, 1984.

19. Erickson E. D.; Zoonosis Update; Streptococcosis, JAVMA 191(11): 1391–1393, 1987.

I claim:

1. A hyperimmune equine antiserum which, when intramuscularly administered to piglets within about 24 hours of birth, provides protection against *Streptococcus suis* infections, essentially without adverse effects on the piglets, wherein the antiserum is reactive with *Streptococcus suis* of a serotype heterologous to the serotype(s) used to immunize the equine.

2. A method of producing an antiserum for use in the treatment or prevention of *Streptococcus suis* infections which comprises immunizing an equine at least four times with the same or different sources of *Streptococcus suis* antigen and recovering the antiserum from the blood of the immunized equine, said antiserum being reactive with *Streptococcus suis* of a serotype heterologous to the serotype(s) used to immunize the equine.

3. A method of protecting piglets from *Streptococcus suis* infections which comprises intramuscularly administering to said piglets, within 24 hours of birth, an antiserum obtained by hyperimmunizing an equine with *Streptococcus suis* antigen and recovering antiserum from the blood of the hyperimmunized equine, whereby the piglets are protected against infection by *Streptococcus suis* of a serotype heterologous to the serotype(s) used to immunize the equine.

4. The antiserum of claim 1 which furthermore is protective for piglets against *Streptococcus suis* of a serotype heterologous to the serotype(s) used to immunize the equine.

5. The antiserum of claim 1, wherein there is a difference in the average clinical score of treated and untreated piglets which is statistically significant at a P of about 0.012 or less.

6. The method of claim 2 wherein the equine is parenterally injected with a source of *Streptococcus suis* type ½ antigen.

7. The method of claim 2 wherein the equine is given at least seven separate doses of a source of *Streptococcus suis* antigen, and wherein said source may be the same or different for each dose.

8. The method of claim 6 in which at least one dose is given subcutaneously.

9. The method of claim 6 in which at least one dose is given intramuscularly.

10. The method of claim 2 wherein at least one source of *Streptococcus suis* antigen is provided by inactivating a *Streptococcus suis* culture with an inactivating agent.

11. The method of claim 10 wherein the inactivating agent is selected from the group consisting of formalin, sodium lauryl sulfate, and heat.

12. The method of claim 2 wherein the equine is immunized with a whole live *Streptococcus suis* culture.

13. The method of claim 2 wherein the source of *Streptococcus suis* antigen is enriched for an M-protein-like substance.

14. The method of claim 2 wherein the equine is injected with a source of *Streptococcus suis* antigen of the type 1 and 2 serotypes and the recovered antiserum is reactive with *Streptococcus suis* of serotype.

15. The method of claim 14 in which the antiserum is also reactive with serotypes 7 and 8.

16. The method of claim 3, wherein there is a difference in the average clinical score of treated and untreated piglets which is statistically significant at a P of about 0.012 or better.

17. The method of claim 3, wherein the infection is caused by a *Streptococcus suis* which antigenically expresses an M-protein-like substance.

* * * * *